(12) United States Patent
Kjellstrom et al.

(10) Patent No.: US 7,192,399 B2
(45) Date of Patent: Mar. 20, 2007

(54) SYSTEM AND METHOD FOR MONITORING MYOCARDIAL PERFORMANCE USING SENSED VENTRICULAR PRESSURES

(75) Inventors: Barbro M. Kjellstrom, Minneapolis, MN (US); Kathryn E. Hilpisch, St. Paul, MN (US); Edward Chinchoy, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 254 days.

(21) Appl. No.: 11/044,645

(22) Filed: Jan. 27, 2005

(65) Prior Publication Data

US 2006/0167514 A1  Jul. 27, 2006

(51) Int. Cl.
*A61B 5/02* (2006.01)
(52) U.S. Cl. .................................................. 600/485

(58) Field of Classification Search ................. 600/485
See application file for complete search history.

(56) References Cited

U.S. PATENT DOCUMENTS 6,792,308 B2 * 9/2004 Corbucci ...................... 607/17
6,986,741 B2 * 1/2006 Poliac et al. ................. 600/485

* cited by examiner

*Primary Examiner*—Robert Pezzuto
*Assistant Examiner*—Yun Haeng Lee
(74) *Attorney, Agent, or Firm*—Girma Wold-Michael; Paul H. McDowall (57) ABSTRACT

A medical device chronically monitors cardiac function in a patient. An input circuit of the medical device receives a pressure signal representative of a pressure sensed within a ventricle of the patient's heart as a function of time. A processor derives from the pressure signal a myocardial performance index based upon pressures in the ventricle. The processor then provides an output based upon the myocardial performance index.

23 Claims, 5 Drawing Sheets

SYSTEM AND METHOD FOR MONITORING MYOCARDIAL PERFORMANCE USING SENSED VENTRICULAR PRESSURES

BACKGROUND OF THE INVENTION

The present invention relates generally to cardiac monitoring, and more particularly, to a method and an apparatus for chronically monitoring a myocardial performance index based upon sensed ventricular pressure waveforms.

The assessment of cardiac performance, or the efficiency of the heart as a pump, is a useful tool for monitoring the progression of a patient's heart disease, as well as for automatically driving any drug and/or electrical therapies of the patient. Cardiac performance is also routinely monitored as part of active clinical interactions, such as in drug titration and in observation of treatment effects.

A decrease in cardiac performance will likely affect the systolic and diastolic phases of a cardiac cycle differently. For that reason, cardiac performance assessment techniques traditionally focused on either the systolic or diastolic functioning of the heart. Common systolic function indicators include ejection fraction (i.e., the portion of blood that is pumped out of a filled ventricle during a contraction), stroke volume (i.e., the amount of blood pumped by the left ventricle of the heart in one contraction), cardiac output (i.e., the amount of blood pumped by the heart per minute), and systolic time interval. Examples of diastolic function indicators include isovolumetric relaxation time interval, isovolumetric contraction time interval, tricuspid/mitral valve inflow velocity patterns, and pulmonary vein/aorta flow.

Prior literature has suggested that combining one or more of the systolic and diastolic function indicators into an algorithm may yield a more effective measurement of the global performance of the heart than achieved by looking solely at one specific timing interval.

One such global cardiac performance indicator is the myocardial performance index (MPI) defined as the sum of the isovolumetric contraction time and the isovolumetric relaxation time divided by the ejection time. Each event of the MPI has been correlated to cellular measures of contractility. The isovolumetric contraction time has been correlated with SERCA++ release, the isovolumetric relaxation with SERCA++ uptake, and the ejection time with state (pre-load and rate) for normalizing isovolumetric contraction and relaxation.

The MPI is derived using echocardiography measurements and has been proven to be a useful predictor of morbidity and mortality in cardiac diseases. Although echocardiography is a noninvasive procedure, and these measurements are easily available, its use in deriving the MPI is limited to applications where the patient is located at a facility with the appropriate equipment, such as a hospital or medical clinic. As such, any attempts to chronically monitor the MPI based upon these echocardiography measurements would be resource exhausting. Moreover, conventional echocardiography techniques make it difficult to evaluate myocardial performance on a beat-by-beat basis, again limiting the usefulness of the MPI.

BRIEF SUMMARY OF THE INVENTION

The present invention is based upon the discovery that, by using sensed ventricular pressures to derive an estimated myocardial performance index, cardiac function can be chronically monitored in heart disease patients, thus enabling better predictions of decompensation in the heart disease patients and/or assessments of an effect of various treatments. The present invention includes a medical device and methods for determining and using estimated myocardial performance index.

A medical device chronically monitors cardiac function in a patient and includes an input circuit and a processor. The input circuit of the medical device receives a signal representative of a pressure sensed within a ventricle of the patient's heart as a function of time. A processor derives from the pressure signal an estimated myocardial performance index based upon pressures in the ventricle. The processor then provides an output based upon the estimated myocardial performance index.

A method for chronically monitoring cardiac function in a patient begins by sensing a blood pressure within a ventricle of the patient's heart as a function of time. From these sensed blood pressures, an estimated myocardial performance index is derived based upon pressures in the ventricle. An output based upon the estimated myocardial performance index is provided.

A method for determining a set of pacing settings for a pacemaker implanted in a patient begins by administering each of a plurality of pacing settings for a period of time. An effect of each pacing setting on an estimated myocardial performance index is monitored. The estimated myocardial performance index is determined from pressure sensed within a ventricle of the patient's heart. Finally, a set of pacing settings is selected from the plurality of pacing settings based upon the estimated myocardial performance index.

DETAILED DESCRIPTION

Figure 1:
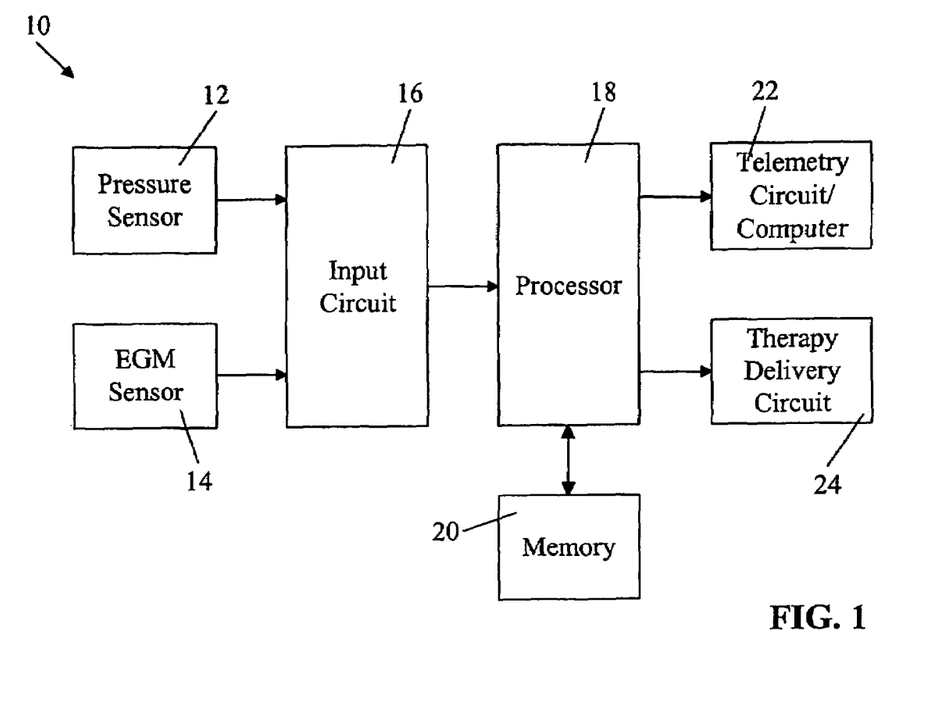
FIG. 1 is a block diagram of a system in accord with the present invention for chronically monitoring a patient's cardiac performance using an estimated myocardial performance index (eMPI).

FIG. 1 is a block diagram of system 10 for chronically monitoring cardiac performance in a patient using an estimated myocardial performance index. System 10 includes pressure sensor 12, electrogram (EGM) sensor 14, input circuit 16, processor 18, memory 20, telemetry circuit/computer 22, and therapy delivery circuit 24. Pressure sensor 12 is located inside a ventricle of the patient's heart to sense blood pressures therein. EGM sensor 14 is located in or near the heart to sense the electrical activity of the heart.

Input circuit 16 is a signal processing circuit that receives a pressure signal representative of blood pressures in the ventricle as a function of time from pressure sensor 12 and an electrical signal representative of the electrical activity in the heart as a function of time from EGM sensor 14. Input circuit 16 may sample, demodulate or otherwise process the signals received from pressure sensor 10 and electrode sensor 12.

From these processed pressure and EGM signals received from input circuit 16, processor 18 derives several hemodynamic parameters defining the operation of the ventricle, including peak positive and negative dP/dt, pre-ejection interval (PEI), and systolic time interval (STI). These hemodynamic parameters are then stored in memory 20 by processor 18 on a beat-by-beat basis, minute-to-minute basis, hour-to-hour basis, or on some other basis.

Processor 18 next uses these hemodynamic parameters to further derive an estimated, or modified, myocardial performance index (eMPI) as a function of these hemodynamic parameters. For instance, the eMPI may be derived as a function of the pre-ejection interval and the systolic time interval. In one example, the eMPI may be derived as:

$$eMPI = PEI \times A / (STI - PEI),$$

where A is a numeric factor. In some embodiments, numeric factor A may be determined such that the product PEI×A approximates a sum of the two isovolumetric intervals. For example, numeric factor A may equal two, such that the eMPI is determined as:

$$eMPI = PEI \times 2 / (STI - PEI).$$

In other embodiments, numeric factor A may be determined to compensate for variations caused in the pressure signal, such as may be caused by transmitted pacing signals. Where processor 18 is capable of deriving a post-ejection interval (PEI2) from the processed pressure signal, the myocardial performance index (MPI) need not be estimated, but may be derived as:

$$MPI = (PEI + PEI2) / (STI - PEI).$$

By chronically monitoring a patient's eMPI, physicians can ascertain an effect of various therapies on the patient, with a decrease in eMPI indicating a positive effect of the therapy on the patient's cardiac performance.

For certain analyses, the eMPI can be normalized using heart rate and/or right ventricular pressure for pre-load adjustments. For example, the eMPI can be normalized for heart rate (HR) by monitoring an index derived by multiplying the eMPI by a factor related to the patient's heart rate. Once such heart-rate normalized index is an eMPI×HR index.

In some embodiments of the present invention, processor 18 next compares the myocardial performance index to a myocardial performance index threshold for the patient stored in memory 20. The patient's myocardial performance index threshold may be determined during an initializing period in which the patient is monitored to establish a baseline, or normal, value for his/her myocardial performance index. The threshold can then be set as a value greater than the baseline, for example, a value 5%–50% greater than the baseline value.

Any increases in the myocardial performance index above the threshold is a predictor of diminished cardiac function and/or worsening heart condition such that additional medical intervention may be warranted. Thus, in one embodiment, processor 18 instructs telemetry circuit 22 to transmit an alert to medical personnel whenever the myocardial performance index rises above the myocardial performance index threshold. Alternately, telemetry circuit 22 may be replaced with a local computer terminal with the capability to display the alert for medical personnel. Telemetry circuit/computer 22 also allows a user, such as the medical personnel, to exchange information, including sensed data and programming parameters, with processor 18.

In other embodiments, processor 18, upon the detection of the myocardial performance index rising above the myocardial performance index threshold, may automatically provide a therapy control signal to therapy delivery circuit 24 to adjust or titrate any of various therapies being administered to the patient. In still other embodiments, the therapy control signal may be provided as a function of the myocardial performance index, regardless of whether the myocardial performance index has risen above the myocardial performance index threshold.

The derivation of the myocardial performance index may also be useful in the optimization of a patient's pacemaker settings. In particular, a set of pacing settings can be selected based upon the monitored effect of various pacing settings of a patient's pacemaker on the myocardial performance index.

The monitoring of the myocardial performance index of a heart failure patient for any of the above-described applications of the present invention can take place in either a system using an implantable medical device (IMD) or in a bedside monitoring medical device for use in a hospital setting.

Figure 2:
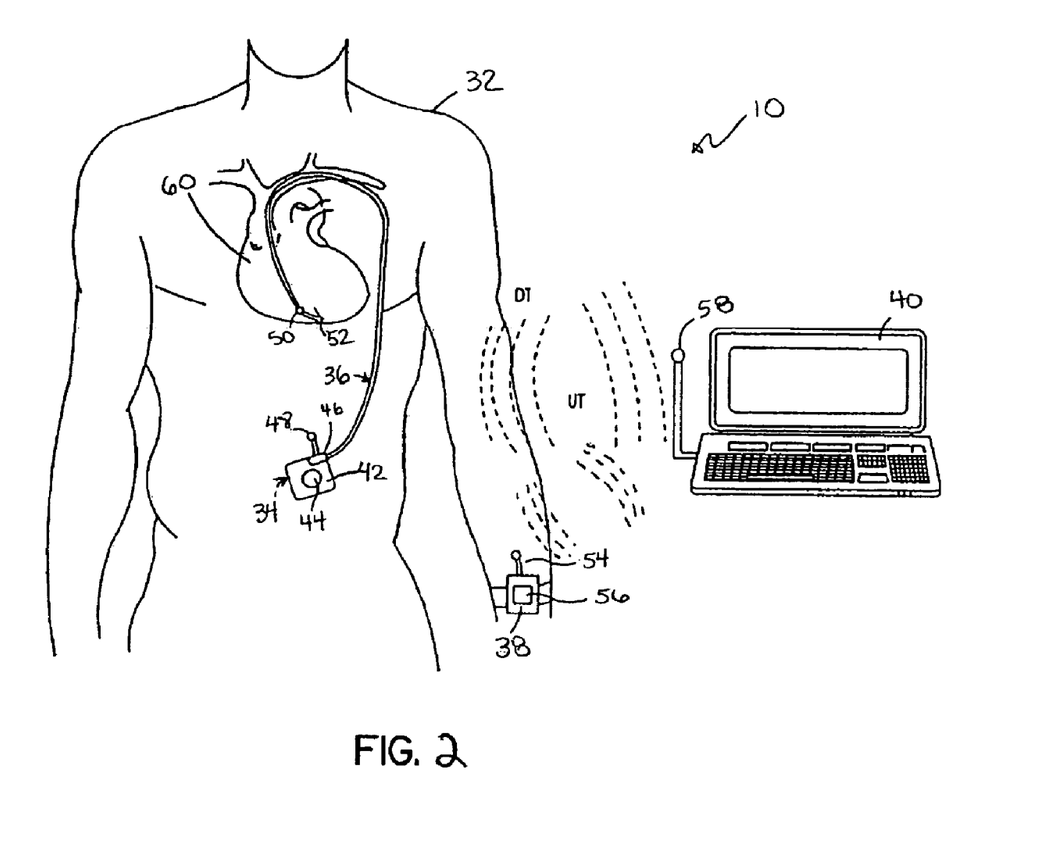
FIG. 2 is a diagram of a system for use in an implantable medical device to chronically monitor the eMPI of a patient.

FIG. 2 is a diagram of system 10 for use in an IMD to chronically monitor the myocardial performance index of patient 32. System 10 includes IMD 34, blood pressure sensor lead 36, atmospheric pressure reference monitor 38, and external computer 40. IMD 34 further includes hermetically-sealed housing 42, activity sensor 44, lead connector header 46, and telemetry antenna 48. Blood pressure sensor lead 36 includes blood pressure sensor 50 and electrogram (EGM) sense electrode 52. Atmospheric pressure reference monitor 38 includes telemetry antenna 54 and optional timepiece function 56. Computer 40 includes telemetry antenna 58.

In one embodiment, IMD 34 is the MEDTRONIC7 CHRONICLE7 implantable hemodynamic monitor (IHM) of the type described in commonly-assigned U.S. Pat. No 5,368,040. IMD 34 is capable of storing data indicative of patient activity level as obtained from activity sensor 44. IMD 34 is further capable of storing blood pressure and heart rate data obtained from blood pressure sensor lead 36 connected to IMD 34 via lead connector header 46. Other possible configurations of the IMD 34 can provide cardioversion/defibrillation and/or pacing therapies requiring additional implantable cardiac leads and electrodes not shown in FIG. 2. IMD 34 may be implanted in the abdomen or upper chest of patient 32.

Blood pressure sensor lead 36 having multiple conductors locates blood pressure sensor 50 and EGM sense electrode 52 within the right ventricle of patient's heart 60. In one embodiment, blood pressure sensor lead 36 is a MEDTRONIC7 Model 4328A blood pressure sensor lead. In this embodiment, blood pressure sensor 50 is a pressure sensing transducer of the type disclosed in commonly-assigned U.S. Pat. No. 5,564,434. Blood pressure sensor lead 36 also incorporates a distal EGM sense electrode 52 and conventional soft pliant tines that provide passive fixation of sense electrode 52 into the ventricular apex in a manner well known in the art. The proximal connector assembly of blood pressure sensor lead 36 is configured in conformance with IS-1 standards for bipolar pacing leads and is fitted into a conforming bore of connector header 46 of IMD 34 in a conventional manner. The EGM of the heart, particularly the R-waves of the PQRST complex, is sensed between EGM sense electrode 26 and an indifferent electrode formed by hermetically-sealed housing 42 of IMD 34 in a conventional unipolar configuration.

Because the CHRONICLE7 Model 9520 IHM measures absolute blood pressure, patient 32 is also provided with atmospheric pressure reference monitor 38 to record atmospheric pressure values. In one embodiment, atmospheric pressure reference monitor 38 is a MEDTRONIC7 Model 2955HF atmospheric pressure reference monitor. Atmospheric pressure reference monitor 38 is schematically depicted as worn on the wrist of patient 32 with optional timepiece function 56, but it may take other portable configurations so that it can accompany patient 32 in her daily routine. The functions of an exemplary atmospheric pressure reference monitor 38 in relation to the IMD 14 and computer 38 are disclosed in commonly-assigned U.S. Pat. No. 5,904,708.

Computer 40 is used to communicate with IMD 34 and atmospheric pressure reference monitor 38 in order to program the operating modes and parameters of IMD 34 or interrogate the data stored in memory of the IMD 34 and atmospheric pressure reference monitor 38. Computer 40 can include a MEDTRONIC7 Model 9790 programmer or a PC with CHRONICLE7 software. Data accumulated by computer 40 is stored in a large FIFO buffer in RAM at a programmable resolution.

Uplink telemetry (UT) and downlink telemetry (DT) transmissions between telemetry antenna 48 of IMD 34 (schematically illustrated as extending from connector header 46 of IMD 34) and telemetry antenna 58 of computer 40 are schematically illustrated in FIG. 2. Similarly, UT and DT transmissions between an telemetry antenna 54 of the atmospheric pressure reference monitor 38 and telemetry antenna 58 of computer 40 are also illustrated in FIG. 2. A direct cable or plug-in connection can be made between ports of atmospheric pressure reference monitor 38 and computer 40 instead of employing the depicted UT and DT transmissions between telemetry antennas 54 and 58 when atmospheric pressure data is to be read from memory in atmospheric pressure reference monitor 38. In conventional use of system 10 depicted in FIG. 2, the storage of absolute blood pressure data and ambient pressure data continues for a period of days, and the data is periodically transmitted to computer 40 during a telemetry session initiated by medical personnel operating the external computer 40. In other embodiments, computer 40 may periodically initiate transfer of data itself. In still further embodiments, IMD 34 and atmospheric pressure reference monitor 38 may communicate with computer 40 in real-time. Computer 40 may also be a remote computer connected to IMD 34 via the Internet.

Figure 3:
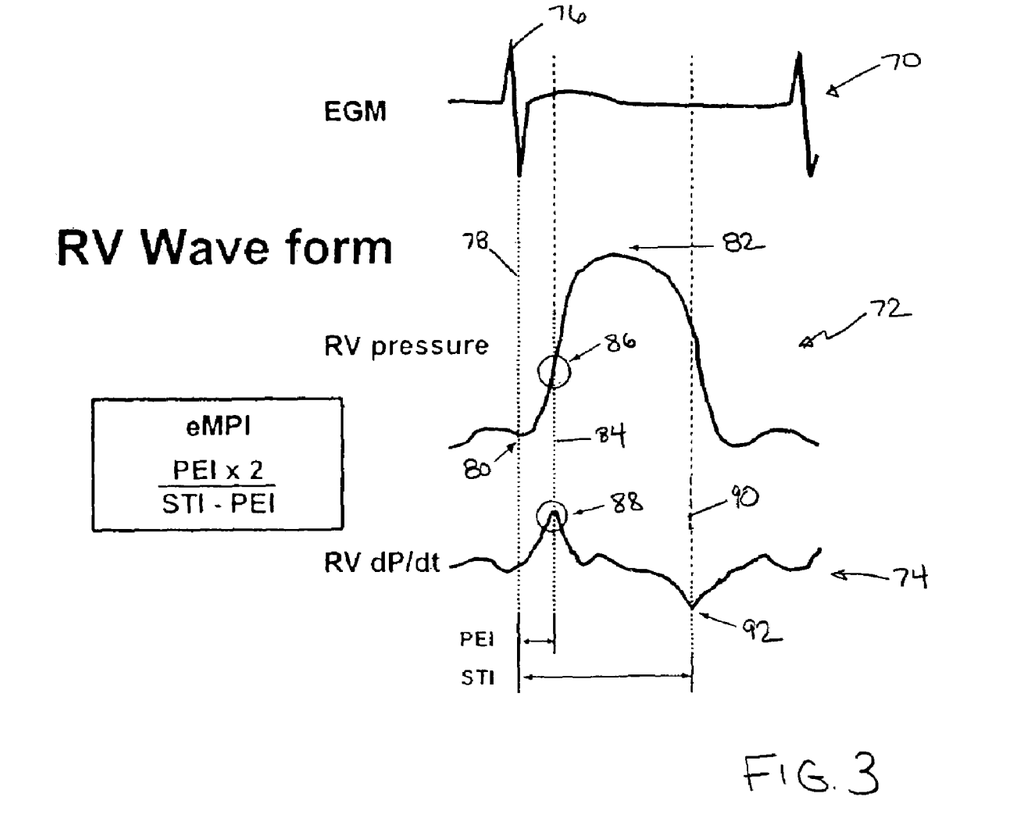
FIG. 3 is a timing diagram providing an overview of a mode of operation of the implantable medical device to determine the eMPI of a patient.

FIG. 3 is a timing diagram providing an overview of a mode of operation of IMD 34 to determine the myocardial performance index. FIG. 3 includes EGM signal 70 representative of the electrical activity in the right ventricle of the heart and right ventricle (RV) pressure signal 72 representative of the fluid pressure in the right ventricle of the heart. FIG. 3 also includes first derivative dP/dt signal 74 derived by IMD 34 for the reasons described below.

R-wave 76 in EGM signal 70 represents ventricular depolarization of the heart, which marks start time 78 of the ventricular contraction. Upon the occurrence of R-wave 76, pressure 72 in the right ventricle is at its minimum pressure 80, which is often referred to as the RV diastolic pressure. Following ventricular depolarization, pressure 72 in the right ventricle increases, eventually reaching its peak pressure 82, which is often referred to as the RV systolic pressure.

For a brief period at the start of ventricular contraction, no blood leaves the right ventricle, and the contraction is isovolumetric. During this isovolumetric contraction, the tricuspid valve an the entry of the right ventricle is closed by backward pressure differential forces. The pulmonary valve at the exit of the right ventricle is likewise closed, as pressure 72 in the right ventricle is insufficient to force blood through it. Consequently, this isovolumetric contraction causes the blood in the right ventricle to undergo increasing pressure 72.

At time 84, pressure 72 in the right ventricle overcomes the pressure in the pulmonary arteries, drives the pulmonary valve open, and ejects blood from the right ventricle into the pulmonary arteries. When the pulmonary valve opens, contraction is no longer isovolumetric. Pressure 72 in the right ventricle, although still increasing due to ventricular contraction, increases at a slower rate. As a result, an inflection point in RV pressure signal 72 occurs at time of valve opening 84. Because the slope of RV pressure signal 72 is at its maximum positive value at the inflection point, positive peak 88 of dP/dt signal 74 corresponds to the inflection point, or time of valve opening 84.

After peaking at RV systolic pressure 82, RV pressure 72 begins to decrease due to the continued ejection of blood from the right ventricle into the pulmonary arteries. At the time 90 of the pulmonary valve closing, the pressure in the right ventricle continues to decrease due to relaxation of the right ventricle. This continued decrease in pressure, however, occurs at a slower rate. Thus, there is another inflection point in RV pressure signal 72 at the time of valve closing 90. Because the slope of RV pressure signal 72 is at its maximum negative value at the inflection point, negative peak 92 of dP/dt signal 74 corresponds to time of closing 90.

From these values, the pre-ejection interval (PEI) can be computed as time of valve opening 84 minus start time of the ventricular contraction 78. Systolic time interval (STI) can be computed as time of valve closing 90 minus start time of ventricular contraction 78. Finally eMPI can be computed as a numerical factor, such as two, times the pre-ejection interval divided by a difference between the systolic time interval and the pre-ejection interval.

In processing these signals, IMD 34 may differentiate RV pressure signal 72 to determine the derivatives of the pressure signal with respect to time. IMD 34 may further apply algorithms to detect the peaks and or zero-crossings of any of these signals or to identify the occurrence of R-wave 76 in the EGM signal 70.

Although shown operating in the right ventricle, the present invention is equally applicable to systems having sensors for measuring blood pressure within the left ventricle. Similar processing as identified above could determine the systolic and diastolic pressures in the left ventricle and to estimate the diastolic pressure in the aorta.

In addition to its application in an IMD, the present invention may also be incorporated in other medical hemodynamic monitoring devices, such as bedside monitoring systems which can simultaneously measure pressures in the right ventricle and the pulmonary arteries and or simultaneously measure pressures in the left ventricle and the aorta. In such system, it is not necessary to estimate pressures in the pulmonary arteries or the aorta. Of course, if the medical hemodynamic monitoring device does not include sensors for the blood vessels, pressures in the blood vessels can be estimated based upon ventricular pressure.

It is also contemplated that in a system having a blood pressure sensor located in a blood vessel rather than a ventricle, estimates of the pressures in the corresponding ventricle may be obtained from the blood vessel pressure signal.

EXAMPLE 1

Figure 4:
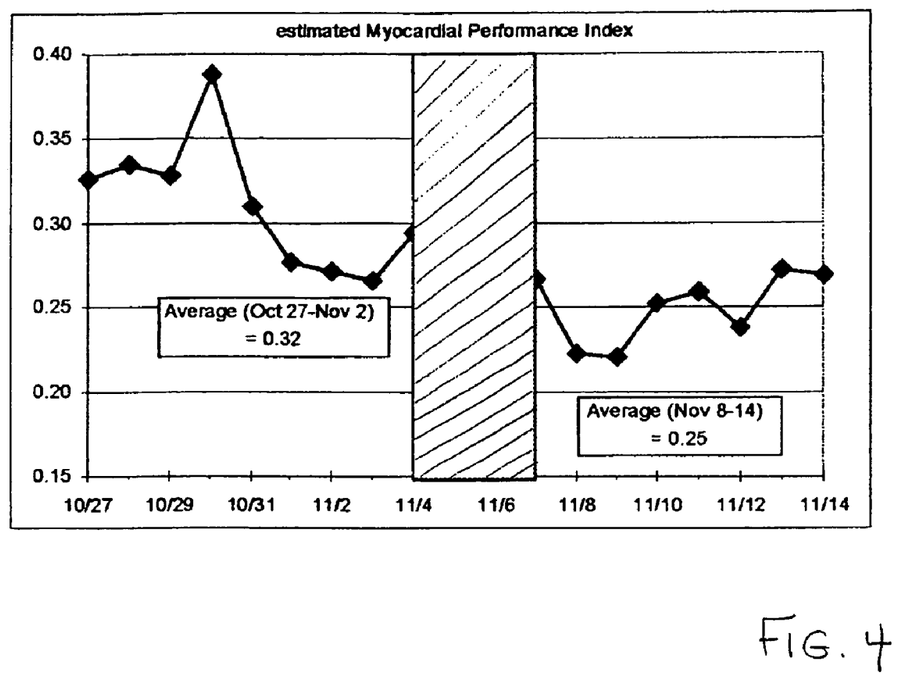
FIG. 4 is a graph illustrating a study in which the eMPI of a patient pulmonary arterial hypertension (PAH) was monitored he underwent a change in treatment.

FIG. 4 is a graph illustrating a study in which the eMPI of a patient pulmonary arterial hypertension (PAH) was monitored as he underwent a change in treatment from inhaled epoprostenol (iloprost) to an endothelin antagonist (bosentan). Both are vasodilating drugs; but, while the inhalation of iloprost has an approximate vasodilatory effect of thirty minutes to two hours, bosentan, administered orally, will have a longer acting vasodilatory effect and should result in lower pulmonary resistance and pressures during a twenty-four hour period. This, in turn, will result in a decrease in the workload of the right ventricle.

The patient was monitored for the week prior to the change in treatment (October 27 to November 2), during which time, the patient's average eMPI was 0.32. The patient underwent the change in treatment from November 3 to November 7 while hospitalized. In the week following the change in treatment (November 8 to November 14), the patient's eMPI averaged 0.25, showing that the drug change positively affected the patient's cardiac performance.

EXAMPLE 2

Figure 5:
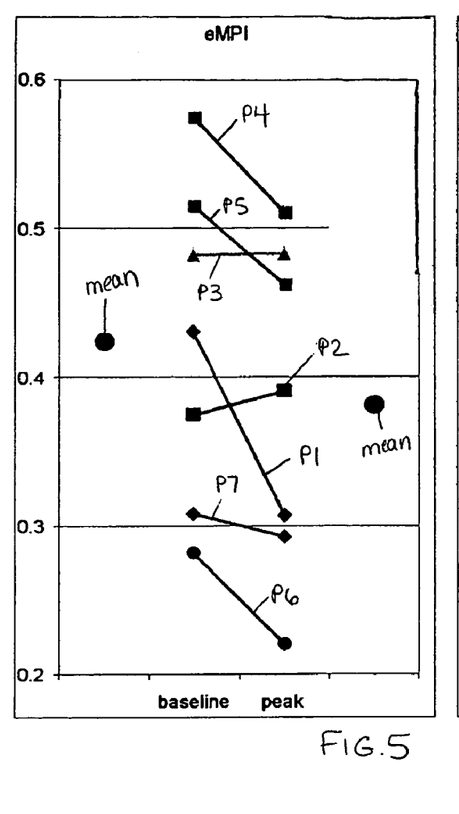
FIGS. 5 and 6 are graphs illustrating a study in which the eMPI and an eMPI×HR indices were monitored in PAH patients starting treatment with endothelin antagonist bosentan.
Figure 6:
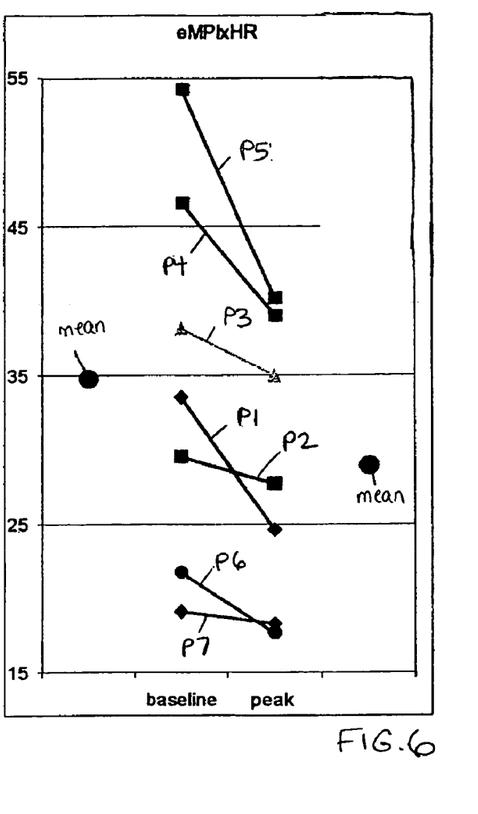

FIGS. 5 and 6 are graphs illustrating a study in which the eMPI (FIG. 5) and eMPIxHR (FIG. 6) indices were monitored in seven PAH patients starting treatment with endothelin antagonist bosentan.

The eMPI and eMPIxHR indices of the study patients was measured at baseline; i.e., five to seven days before the start of treatment. These baselines values were then compared to values obtained at peak, i.e., during the fourth week after a maximal dose (a target dose or a maximal tolerated dose) was reached. All calculations were made from the daily mean of the median values recorded. Table 1 below, which is graphically represented in FIG. 5, reports the measurements of the eMPI recorded at baseline and peak for the study patients, along with a percent change reported for each patient. A mean of all patients was also computed, with the mean eMPI recorded at baseline being 0.42, and the mean eMPI recorded at peak being 0.38 B a percent change of negative 10.1.

TABLE 1

| | eMPI | | | | | | | |
|---|---|---|---|---|---|---|---|---|
| | P1 | P2 | P3 | P4 | P5 | P6 | P7 | Mean |
| baseline | 0.43 | 0.37 | 0.48 | 0.57 | 0.52 | 0.28 | 0.31 | 0.42 |
| peak | 0.31 | 0.39 | 0.48 | 0.51 | 0.46 | 0.22 | 0.29 | 0.38 |
| % change | −28.6 | 4.4 | 0.3 | −11.1 | −10.3 | −22.2 | −5.0 | −10.1 |

The eMPIxHR index was designed to compensate for variations in daily activity. Table 2 below, which is graphically represented in FIG. 6, reports these measurements of the eMPIxHR index recorded at baseline and peak for the study patients, along with a percent change reported for each patient. A mean of all patients was also computed, with the mean eMPIxHR recorded at baseline being 34.71, and the mean eMPIxHR recorded at peak being 28.95 B a percent change of negative 16.6.

TABLE 2

| | eMPIxHR | | | | | | | |
|---|---|---|---|---|---|---|---|---|
| | P1 | P2 | P3 | P4 | P5 | P6 | P7 | Mean |
| baseline | 33.50 | 29.59 | 38.17 | 46.61 | 54.23 | 21.73 | 19.12 | 34.71 |
| peak | 24.63 | 27.63 | 34.96 | 39.12 | 40.26 | 17.65 | 18.30 | 28.95 |
| % change | −26.5 | −6.3 | −8.4 | −16.1 | −25.8 | −18.8 | −4.3 | −16.6 |

When looking at the eMPI alone, patients P1, P3, P4, P5, and P6 were considered to have a positive treatment effect, while patients P2 and P7 had no or negative effect. When the eMPIxHR index is used, all patients appear to have benefitted from the treatment; however, the positive change of the index varied. Four patients had changes of 15% or more, and, of those, two changed more than 25%.

P3, who was considered to have a positive treatment effect by other methods evaluating pressure performance, but whose percent changes in the eMPI and eMPIxHR indices were less than 10%, has recently undergone another treatment change B this time to intravenous epoprostenol (FLOLAN7) due to a lack of improvement in symptoms.

Patients P1 and P5 experienced their lowest ventricular pressures at a dose different than the maximal dose. The lowest pressures for patient P1 were experienced at a dosage of 250 mg/day. A slight increase, four percent, was seen in right ventricle systolic pressure and the mean pulmonary artery pressure when the drug dose was increased to 500 mg/day. However, the pressures were 12–13% lower at maximal dose than at baseline and activity counts were higher at the maximal dose than at 250 mg/day. The eMPI× HR decreased 26% from baseline to maximal dose but only 18% from baseline to 250 mg/day.

P5 has the lowest pressure at a dosage of 125 mg/day. When the dose was increased to 250 mg/day (maximal dose), the pressures rose approximately 8%. Still, at maximal dose, the right ventricle systolic pressure and the mean pulmonary artery pressure were down 9% and 13%, respectively, from baseline, and activity counts were at their highest value. The eMPI×HR index was lowest at a dosage of 125 mg/day, a decrease of 30% from baseline compared to a 26% decrease from baseline at maximal dose. Patient P5's symptoms improved with bosentan treatment, but the right ventricular and pulmonary pressures remained high. After seven months at maximal dose bosentan, a calcium channel blocker (NORVASC7) was started. When patient P5 had reached a stable dose of 10 mg/day, the data from the fourth week on that dose was analyzed. The right ventricular systolic pressure and mean pulmonary artery pressures had decreased almost 40% from baseline, activity was up 77%, and eMPI×HR had decreased 41%.

Although the small PAH population tested was not large enough to draw conclusions, the study provides incentive to continue observing the eMPI and eMPI×HR indices when monitoring the effects of various treatments on a patient's cardiac function.

In sum, the present invention is a system and a method for chronically monitoring cardiac function in heart disease patients, thus enabling better predictions of decompensation. In particular, a pressure signal is sensed in a ventricle. From that pressure signal, an estimated myocardial performance index determined as a function of these sensed ventricular pressures. This estimated myocardial performance index may be used in monitoring the effects of new drug and/or electrical treatments. When compared with a patient specific threshold, this estimated myocardial performance index serves to predict worsening heart disease and to further allow for automatic or physician-prescribed modification of the patient therapies to address the cause of the worsening disease.

Although the present invention has been described with reference to preferred embodiments, workers skilled in the art will recognize that changes may be made in form and detail without departing from the spirit and scope of the invention.

What is claimed is:

1. A medical device for chronically monitoring cardiac function in a patient, comprising:
    an input circuit that receives a pressure signal representative of a pressure sensed within a ventricle of a heart as a function of time; and
    a processor that derives from the pressure signal a myocardial performance index based upon pressures in the ventricle and provides an output based upon the myocardial performance index.

2. A medical device according to claim 1 and further comprising a blood pressure sensor located in the ventricle for providing the pressure signal to the input circuit.

3. A medical device according to claim 2 wherein the blood pressure sensor is located in the right ventricle.

4. A medical device according to claim 1 wherein the input circuit also receives an electrical signal representative of electrical activity in the heart as a function of time.

5. A medical device according to claim 4 wherein the processor determines the myocardial performance index as a function of a pre-ejection interval and a systolic time interval, the intervals being derived from the pressure and electrical signals.

6. A medical device according to claim 5 wherein the input circuit also receives a heart rate signal representative of a heart rate of the patient as a function of time, and wherein the processor further determines a heart-rate normalized myocardial performance index as a function of the myocardial performance index and the heart rate.

7. A medical device according to claim 4 wherein the processor determines the myocardial performance index as a function of a pre-ejection interval, a post-ejection interval, and a systolic time interval, the intervals each being derived from the pressure and electrical signals.

8. A medical device according to claim 1 and further comprising a memory for storage of a myocardial performance index threshold determined for the patient, wherein the processor detects when the myocardial performance index is greater than the myocardial performance index threshold.

9. A medical device according to claim 8 wherein the output provided by the processor is a warning signal indicating that the myocardial performance index has risen above the myocardial performance index threshold.

10. A medical device according to claim 1 wherein the output provided by the processor is a therapy control signal based upon the myocardial performance index, the control signal being provided to adjust a therapy of the patient.

11. A medical device according to claim 1 wherein the output is a waveform representative of the myocardial performance index as a function of time.

12. A method for chronically monitoring cardiac function in a patient, the method comprising:
    sensing a blood pressure within a ventricle of the patient's heart as a function of time;
    deriving from the sensed blood pressure a myocardial performance index based upon pressure in the ventricle; and
    providing an output based upon the myocardial performance index.

13. A method according to claim 12 wherein the blood pressure is sensed by a blood pressure sensor adapted to be located in the ventricle.

14. A method according to claim 13 wherein the ventricle comprises the right ventricle.

15. A method according to claim 12 and further comprising:
    obtaining an electrical signal representative of the electrical activity in the heart as a function of time.

16. A method according to claim 15 wherein deriving a myocardial performance index comprises:
    determining from the pressure signal and the electrical signal a pre-ejection interval and a systolic time interval; and
    determining the myocardial performance index as a function of the pre-ejection interval and the systolic time interval.

17. A method according to claim 16 and further comprising:
    obtaining a heart rate signal representative of a heart rate of the patient; and
    determining a heart-rate normalized myocardial performance index as a function of the myocardial performance index and the heart rate.

18. A method according to claim 15 wherein deriving a myocardial performance index further comprises:
    determining from the pressure signal and the electrical signal a pre-ejection interval, a post-ejection interval, and a systolic time interval; and
    determining the myocardial performance index as a function of the pre-ejection interval, the post-ejection interval, and the systolic time interval.

19. A method according to claim 12 and further comprising:
    determining a myocardial performance index threshold for the patient; and
    detecting when the myocardial performance index is greater than the myocardial performance index threshold.

20. A method according to claim 19 wherein providing an output based upon the myocardial performance index comprises:
    providing a warning signal upon the detection of the myocardial performance index rising above the myocardial performance index threshold.

21. A method according to claim 12 wherein providing an output based upon the myocardial performance index comprises:
    providing a therapy control signal based upon the myocardial performance index to adjust a therapy of the patient.

22. A method according to claim 12 wherein providing an output based upon the myocardial performance index comprises:
    outputting a waveform representative of the myocardial performance index as a function of time.

23. A method for determining a set of pacing settings for a pacemaker implanted in a patient, the method comprising:
    administering a plurality of pacing settings, each pacing setting being administered for a period of time;
    monitoring an effect of each pacing setting on a myocardial performance index, the myocardial performance index being determined from a pressure signal sensed from within a ventricle of the patient's heart; and
    selecting from the plurality of pacing settings a set of pacing settings based upon the myocardial performance index.

* * * * *